(12) United States Patent
Manos et al.

(10) Patent No.: US 7,810,447 B2
(45) Date of Patent: Oct. 12, 2010

(54) ARTICULATING PAPER COATING DISPENSER AND METHOD

(76) Inventors: Deborah Manos, 1009 Sunningdale Dr., Gross Point Woods, MI (US) 48236; Harry-George T. Manos, 9675 Mariner Village Ct., Las Vegas, NV (US) 89147-8060; Joseph R. Mackenroth, III, Mindtek Intellectual Properties, Ltd., P.O. Box 10523, New Orleans, LA (US) 70181

( * ) Notice: Subject to any disclaimer, the term of this patent is extended or adjusted under 35 U.S.C. 154(b) by 1178 days.

(21) Appl. No.: 11/306,732

(22) Filed: Jan. 9, 2006

(65) Prior Publication Data

US 2006/0166164 A1    Jul. 27, 2006

Related U.S. Application Data

(60) Provisional application No. 60/593,375, filed on Jan. 8, 2005.

(51) Int. Cl.
*B05C 3/00* (2006.01)
(52) U.S. Cl. .............................. 118/429; 433/70; 433/71
(58) Field of Classification Search ................. 118/429, 118/76–78; 433/70, 71; 401/10; 15/209.1, 15/210.1; 206/233, 237; 132/286, 317–318
See application file for complete search history.

(56) References Cited

U.S. PATENT DOCUMENTS

| | | | | |
|---|---|---|---|---|
| 1,978,716 A | * | 10/1934 | Morehouse | 401/10 |
| 2,330,257 A | * | 9/1943 | Bailey | 28/118 |
| 3,731,687 A | * | 5/1973 | Glassman | 604/379 |
| 3,813,781 A | | 6/1974 | Forgione | |
| 3,959,881 A | | 6/1976 | Kokal, Jr. | |
| 4,547,155 A | | 10/1985 | Adler | |
| 5,326,261 A | | 7/1994 | Rains | |
| 5,395,239 A | | 3/1995 | Komatsu et al. | |
| 5,676,647 A | * | 10/1997 | Cimber | 604/11 |
| 5,941,150 A | | 8/1999 | Kropf et al. | |
| 6,592,540 B2 | * | 7/2003 | DeCarlo | 604/12 |

* cited by examiner

*Primary Examiner*—Brenda A Lamb
(74) *Attorney, Agent, or Firm*—Kenehan & Lambertsen, Ltd.; John C. Lambertsen

(57) ABSTRACT

A strip of dental articulating paper is held pincer-like between two biased lateral edges of an outer housing. A grip head overlying a liner protects one lateral edge of the dental articulating paper, with a linear tracing of petroleum jelly formed on the liner adjacent exposed surfaces on both sides of the dental articulating paper. During storage, the grip head is received by and between the two biased lateral edges of the housing. Immediately prior to use, the dental professional slowly removes the grip head from the housing, with the biased lateral edges pressing against the sides of the withdrawing articulating paper, spreading an even, thin film of petroleum jelly over the surfaces thereof.

10 Claims, 2 Drawing Sheets

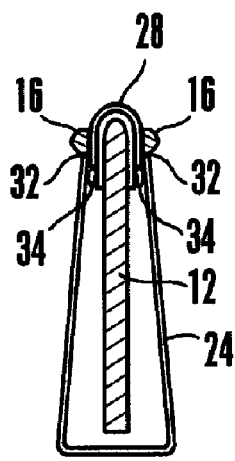
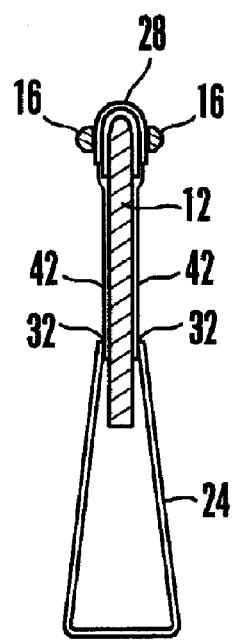
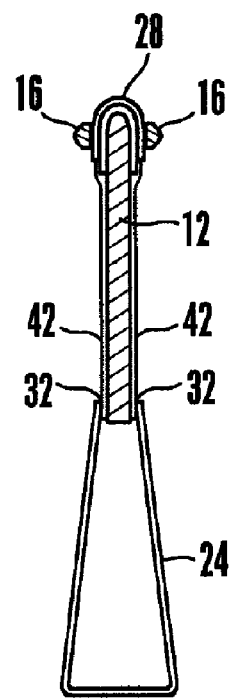
Figure 3A  Figure 3B  Figure 3C
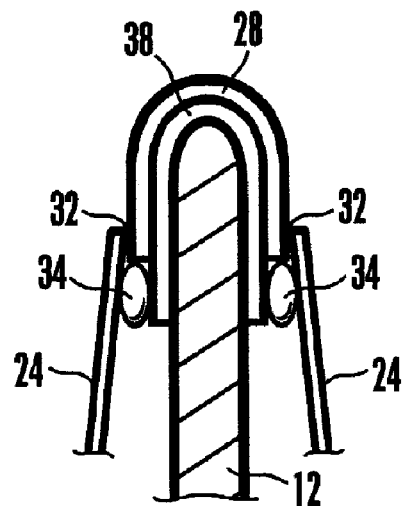
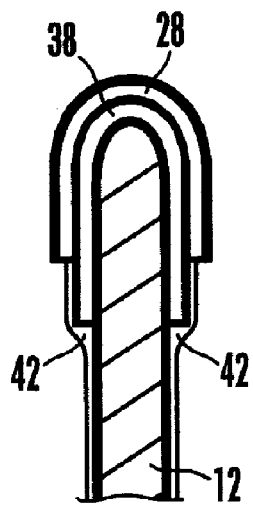
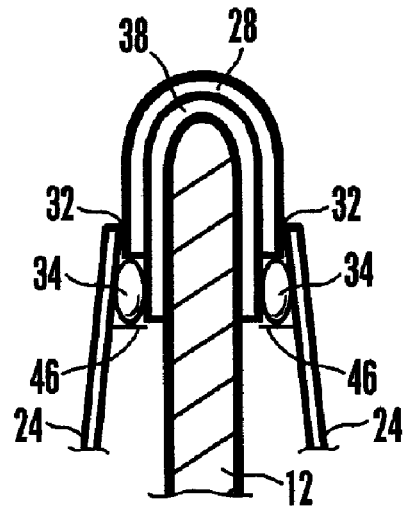
Figure 4A  Figure 4B  Figure 5

ARTICULATING PAPER COATING DISPENSER AND METHOD

CROSS-REFERENCE TO RELATED APPLICATION

This application claims the benefit of U.S. Provisional Patent Application, Ser. No. 60/593,375, filed Jan. 8, 2005.

FIELD OF THE INVENTION

The present invention relates to personal tape dispensers, and more particularly, to hand-held personal dispensers for holding and dispensing dental articulating paper. More specifically, the present invention relates to a hand-held dispenser for dental articulating paper that applies a coating to the paper as it is dispensed.

DESCRIPTION OF THE PRIOR ART

Teeth play an essential role in the human digestive system. By reducing food in the mouth to smaller-sized particles there is a more efficient mix of food with saliva, food may be more comfortably swallowed, and the smaller food particles can be more efficiently acted upon by digestive enzymes. Ridges, slopes, peaks, and valleys characterize the posterior teeth, enhancing the grinding and crushing action applied to food placed between the teeth of the upper and lower jaws.

Changes in mating surfaces can result in the formation of "high spots" or "prematurities," areas of premature tooth contact. One or a few teeth making impact prior to the widely distributed contacts of normal occlusion impairs the ability to adequately chew foods. Additionally, this mal-occlusion normally results in tooth pain, which further impairs chewing performance.

Prematurities can result from normal wear and the positional shifting of teeth. More commonly they are man-made and are created as an inevitable part of making false teeth, crowns, and fillings. Regardless of the cause, it is important that prematurities be addressed, which means they must first be located and then removed by grinding.

Improvements in sensor technology and software have resulted in sophisticated occlusal analyzers that locate problematic contacts and contact force concentrations. The T-SCAN® occlusal analyzer offered by Tekscan, Inc., of South Boston, Mass. is an example of such a device. However, the majority of dental professionals continue to make use of dental articulating paper. Conventional dental articulating paper has a paper or polymer support layer upon which one or two layers of a carbon material is attached.

The carbon material is frequently encapsulated within a protective micro-sphere of wax or plastic to prevent undesired marking during setup. The paper is placed between the occlusal area of interest and the opposing teeth are brought together as the patient bites down on the paper. As the paper is crushed between the opposing bite surfaces, the carbon (or other) pigments of the articulating paper mark the locations of greater applied pressure.

Achieving visible markings on moist occlusal surfaces has continued to plague articulating paper technology. It is theorized that moisture on the tooth interacts with the plastic or wax protective layer of the carbon material to interfere with marking process. Such interference tends to be somewhat erratic, with the carbon material sticking in some places and not in others. This unpredictable carbon marking adhesion behavior provides the dental practitioner with an incomplete contact assessment and thus poor resolution of tooth surface contact.

A thin layer of petroleum jelly has been found to minimize the adhesion marking problem for moist tooth surfaces. Utilizing such a coating has resulted in a transfer of carbon to the occlusal teeth in a manner that provides greater coverage and increased detail in comparison to uncoated articulating paper.

It is believed that the petroleum jelly displaces resident tooth surface moisture, preventing the wax-encapsulated carbon particles from being displaced. The petroleum jelly is far more compatible with the wax material than is water. Moisture on tooth surfaces no longer laterally displaces the wax/carbon micro-spheres, enabling a greater number of carbon particles to adhere to tooth surfaces and thus a greater resolution of tooth surface contact.

The manual coating of the articulating paper with petroleum jelly has drawbacks, one obvious, the other, less so. The process of applying petroleum jelly to both sides of articulating paper using gloved fingers is messy and the subsequent use of the now-greasy gloves is unpleasant for a patient. In addition, using jellied gloves invites mishaps as dental tools slip from the hands of the dental professional.

Pre-coating the articulating paper seems logical, but runs afoul of an unanticipated chemical interaction between the petroleum jelly and wax microcapsules. The wax, also a petroleum product is soluble in the petroleum jelly. Over a short period of time after exposure to the jelly the wax microspheres dissolve. The resulting coating on the articulating paper is best described as "pasty goo," rendering the articulating paper unusable.

SUMMARY OF THE INVENTION

It is an object of the present invention to provide a coating dispenser for dental articulating paper that coats the paper as it is withdrawn for use on a patient.

A dental articulating paper coating dispenser comprises an outer housing having a lateral opening formed therein; a strip of dental articulating paper removable received within said housing. A grip head is attached to said strip of dental articulating paper and is positioned within said outer housing in a manner such that a portion of said grip head extends through said lateral opening and projects beyond an outer surface of said housing. A linear tracing of petroleum jelly is formed at a location within said outer housing, that location is substantially adjacent to but spaced from said strip of dental articulating paper.

These and various other advantages and features of the present invention are pointed out with particularity in the claims. Reference should also be had to the drawings which form a further part hereof, as well as to the accompanying descriptive matter in which are illustrated and described various examples in accordance with the invention.

BRIEF DESCRIPTION OF THE DRAWINGS

FIGS. 3A-3C are a sequence of elevation views, in cross-section along line 3-3 of FIG. 2, showing a manner of removing a segment of articulating paper from within an articulating paper coating dispenser in accordance with the present invention.

FIG. 4A is a partial enlarged view, in cross-section, showing a stored arrangement of a grip head as received within an articulating paper coating dispenser in accordance with the present invention.

FIG. 4B is a partial enlarged view, in cross-section, showing a grip head and attached articulating paper upon removal from an articulating paper coating dispenser in accordance with the present invention.

FIG. 5 is a partial enlarged view, in cross-section, showing an alternative stored arrangement of a grip head as received within an articulating paper coating dispenser in accordance with the present invention.

DETAILED DESCRIPTION OF THE PREFERRED EMBODIMENTS

Figure 1:
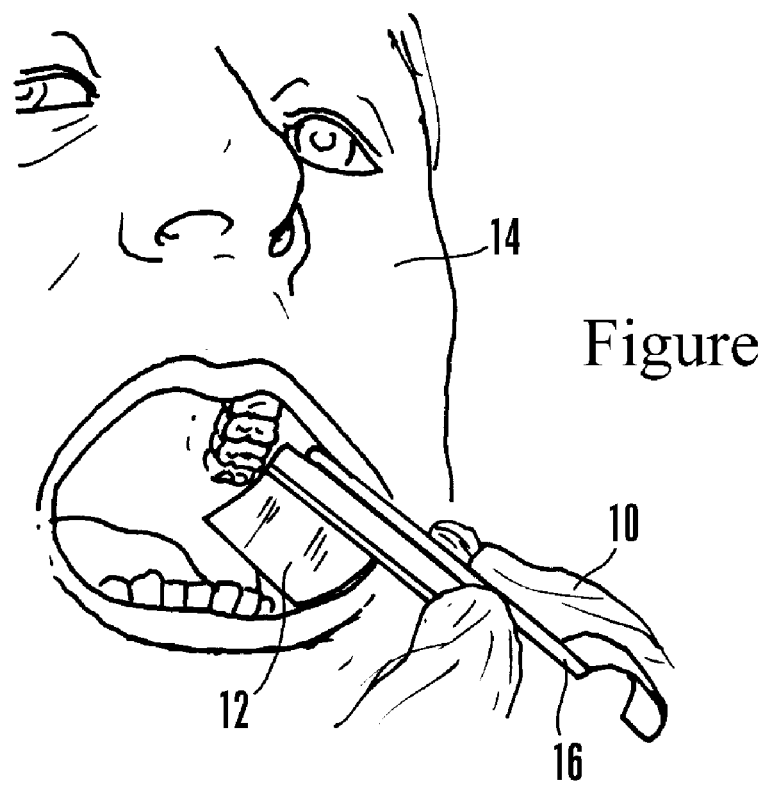
FIG. 1 is a partial perspective view showing use of articulating paper within the mouth of a patient.

Reference is now made to the drawings wherein like numerals refer to like parts throughout. In FIG. 1, a dental professional 10 is shown positioning an articulating paper 12 within the mouth of a patient 14. An articulating paper (Miller) forceps 16 are used by the dental professional 10 to assist in the positioning and removal of the articulating paper 12.

Figure 2:
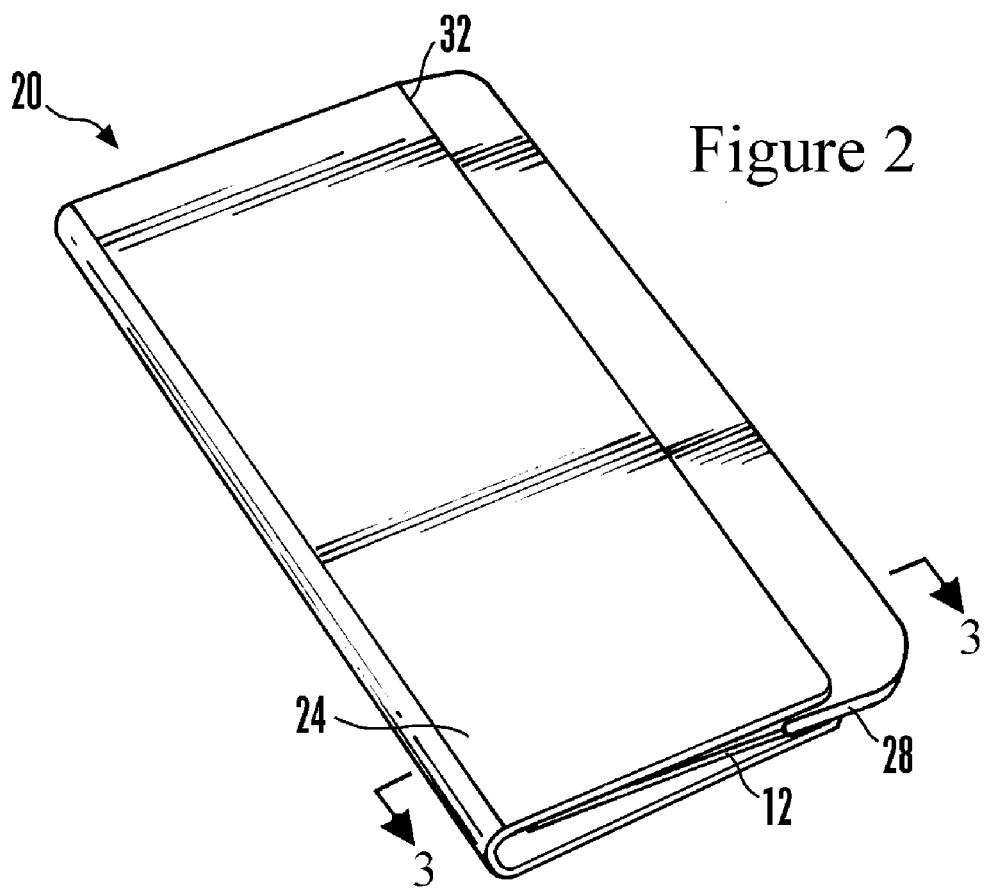
FIG. 2 is a perspective view showing an articulating paper coating dispenser in accordance with the present invention.

As shown in FIG. 2, in accordance with the present invention an articulating paper coating dispenser 20 is provided. The articulating paper 12 is substantially received within an outer housing 24. A grip head 28 is attached to a lateral edge of the articulating paper and projects from the outer housing 24 at a lateral opening 32. The grip head 28 is preferably fabricated out of a more rigid material than the articulating paper 12 and is utilized to form a secure, sealed relationship between the articulating paper 12 and the outer housing 24.

The grip head 28 also provides a convenient handle manipulating the articulating paper 12, whether when removing the articulating paper 12 from the outer housing 24 through the lateral opening 32 or during its employ to obtain occlusal registration information from a patient using the forceps 16 (as shown in FIG. 1). The extraction process is best described with reference to FIGS. 3A-3C.

In FIG. 3A the articulating paper 12 is fully received within the outer housing 12. The grip head 28 is preferably removably attached to the outer lateral edges of the outer housing 12 utilizing, for example, an adhesive or ultrasonic welding. A linear tracing of petroleum jelly 34 is located within the outer housing 16 and adjacent its location of linear attachment to the grip head 28.

As is best shown in the enlarged view of FIG. 4A, a head liner 38 is preferably located between the grip head 28 and the articulating paper 12. To prevent the possible degradation of the articulating paper 12 due to extended contact with petroleum jelly, the linear tracing of petroleum jelly 34 is received by a head liner 38. As so arranged, the articulating paper coating dispenser is substantially shelf-stable.

When need of articulation paper arises, the dental professional 10 (not shown in FIGS. 3 and 4) grasps the grip head 28, either using his/her hands or using the forceps 16, and breaks the releasable attachment of the grip head 28 to the outer housing 24. Such manipulations might consist of bending or rocking the grip head 28 relative to the outer housing 24, until the grip head 28 is separated from the outer housing 24.

Turning to FIGS. 3B and 4B, the articulating paper 12 is then extracted from the outer housing 24 through the lateral opening 32—most conveniently by the continued pulling on the grip head 28 by the dental professional 10 using the forceps 16. As the articulating paper 12 is withdrawn from the outer housing 24, the linear tracing of petroleum jelly 34 is smeared over the outer surface of the articulating paper 12 forming a petroleum jelly coating 42 thereon.

In a presently preferred embodiment the outer housing 24 is configured in a manner that results in a biasing force applied against the grip head 28 and the articulating paper 12 by both lateral sides of the outer housing 24 at the lateral opening 32. The provision of such force is advantageous towards obtaining the uniform coating 42 of the petroleum jelly across the entire surface of the articulating paper 12.

An alternative embodiment is shown in FIG. 5, where a pair of barrier ribs 46 project out from opposing inside surfaces of the outer housing 24 at a location substantially adjacent the lateral opening 32. Each of the barrier ribs 46 laterally extend the length of the outer housing 24 and cooperate with a proximate surface of the head liner 38 to compartmentalize the linear tracing of petroleum jelly 38. As mentioned previously, articulating paper cannot survive long-term contact with petroleum jelly. The barrier ribs 46 function to contain the petroleum jelly as positioned against the head liner 38, blocking unwanted migration of the petroleum jelly during storage.

In a preferred embodiment, the articulating paper coating dispenser—both the outer housing 24 and the grip head 28 are fabricated primarily out of plastic through an extrusion process. The articulating paper 12 is preferably obtained from a commercial source, such as Ardent International, Inc., 400 Executive Boulevard, Ossining, N.Y. 10562. Likewise the petroleum jelly used is commercial grade, such as VASELINE® brand petroleum jelly, which is commonly available.

In a presently preferred embodiment, the articulating paper coating dispenser 20 has overall dimensions of 1 inch by 2.25 inches. The outer housing 24 has dimensions of 0.84 inches by 2.25 inches, with a thickness of 0.16 inches at the base, narrowing to 0.06 inches at the lateral opening 32. The articulating paper 12 has a length of 2.25 inches and width 0.75 inches, with the grip head 28 receiving the articulating paper having dimensions 0.376 inches by 2.25 inches, and thickness 0.61 inches.

The head liner 38 is preferably fabricated out of adhesive plastic tape and extends to cover approximately 0.24 inches on both sides of the articulating paper. The grip head 28 likewise extends down approximately 0.158 inches on both sides of the articulating paper, leaving approximately 0.18 inches of the head liner 38 exposed to receive the linear tracing of petroleum jelly 34. When used, the barrier rib 46 is formed approximately 0.181 inches from the lateral opening, and extends outward a distance of approximately 0.025 inches to substantially contact the head liner 38. As the articulating paper is removed from the outer housing 24, the approximately less than 1 ounce of petroleum jelly is smeared by the biased walls of the outer housing 24 to create a coating 42 of approximately 0.002 inches in thickness over both exposed surfaces of the articulating paper.

Our invention has been disclosed in terms of a preferred embodiment thereof, which provides an articulating paper coating dispenser that is of great novelty and utility. Various changes, modifications, and alterations in the teachings of the present invention may be contemplated by those skilled in the art without departing from the intended spirit and scope thereof. It is intended that the present invention encompass such changes and modifications.

What is claimed is:

1. A dental articulating paper coating dispenser, comprising:
    an outer housing having a lateral opening formed therein;
    a strip of dental articulating paper removably received within said housing;
    a grip head attached to said strip of dental articulating paper, said grip head and said strip of dental articulating paper positioned within said outer housing in a manner such that a portion of said grip head extends through said lateral opening and projects beyond an outer surface of said housing; and a supply of petroleum jelly is arranged at a location within said outer housing that is substantially adjacent to but spaced from said strip of dental articulating paper.

2. A dental articulating paper coating dispenser according to claim 1, and further comprising a head liner attached to said strip of dental articulating paper at a location intermediate said grip head and said dental articulating paper.

3. A dental articulating paper coating dispenser according to claim 2, wherein said supply of petroleum jelly is formed on said head liner.

4. A dental articulating paper coating dispenser according to claim 3, wherein said grip head extends through said lateral opening in a manner such that said outer housing exerts a biasing force against said grip head.

5. A dental articulating paper coating dispenser according to claim 4, wherein said supply of petroleum jelly is located adjacent said lateral opening in a manner such that said outer housing exerts a biasing force against said supply of petroleum jelly upon removal of said dental articulating paper from said outer housing.

6. A paper coating dispenser, comprising:

an outer housing having a first lateral side and a second lateral side, both of which terminate in a lateral edge, said first and said second lateral edges biased towards one another and together form a lateral opening in said outer housing;

a lateral paper strip substantially received within said outer housing and partially extending through said lateral opening in a manner such that said lateral paper strip is selectively removable therefrom;

a liner attached to a lateral edge of said lateral paper strip;

a supply of petroleum jelly is arranged within said outer housing at a location substantially adjacent said lateral opening in said outer housing, wherein said supply of petroleum jelly is applied onto said liner, and wherein said liner extends along and over said lateral edge, covering a portion of said lateral paper strip on both sides thereof, and wherein said supply of petroleum jelly is arranged on said liner, extending along both sides of said lateral paper strip; and a grip head attached to and overlying in part said liner along said lateral edge of said lateral paper strip.

7. A paper coating dispenser according to claim 6, wherein said grip head is received by and between said first and said second lateral edges, extending through said lateral opening when said paper coating dispenser is in a stored configuration.

8. A paper coating dispenser according to claim 7, and further comprising a barrier rib formed on and projecting from each of said lateral sides of said outer housing at a location proximate to each of said lateral edges thereof.

9. A paper coating dispenser according to claim 8, wherein said barrier ribs and said liner cooperatively prevent contact between said supply of petroleum jelly and an exposed surface of said paper strip when said paper coating dispenser is in a stored configuration.

10. A paper coating dispenser according to claim 9, wherein said lateral paper strip comprises dental articulating paper.

* * * * *